Figure 1:
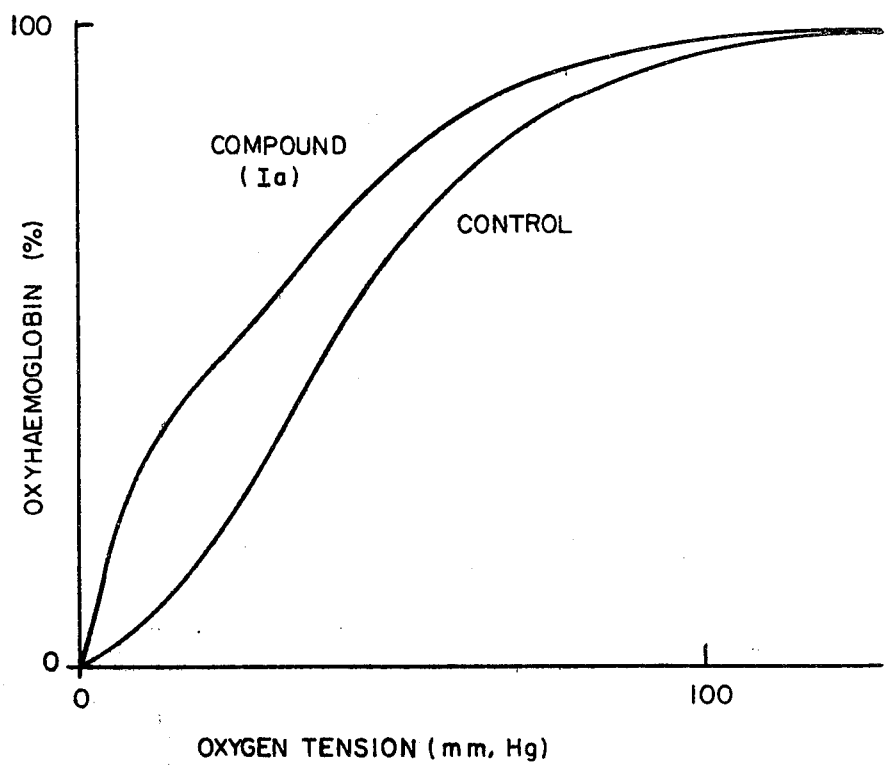

United States Patent [19]

Kneen

[11] 4,410,537

[45] Oct. 18, 1983

[54] PHARMACEUTICAL ETHERS

[75] Inventor: Geoffrey Kneen, Bromley, England

[73] Assignee: Burroughts Wellcome Co., Research Triangle Park, N.C.

[21] Appl. No.: 271,950

[22] Filed: Jun. 9, 1981

Related U.S. Application Data

[63] Continuation of Ser. No. 163,589, Jun. 27, 1980, abandoned.

[30] Foreign Application Priority Data

Jun. 29, 1979 [GB] United Kingdom ............... 7922781

[51] Int. Cl.$^3$ .................. A61K 31/41; A61K 31/275; C07C 121/75; C07D 257/04
[52] U.S. Cl. ............................... 424/269; 260/465 F; 260/501.1; 548/253; 560/53; 562/463; 562/464; 564/169; 424/304; 424/308; 424/316; 424/317; 424/324
[58] Field of Search .................. 260/465 F, 501.1; 560/53; 562/463, 464; 564/169; 548/253; 424/253, 269, 304, 308, 316, 317, 324

[56] References Cited

U.S. PATENT DOCUMENTS 3,914,286 10/1975 Mieville ........................ 562/464 X
4,137,309 1/1979 Van Duzee ........................ 424/204

FOREIGN PATENT DOCUMENTS 2523108 12/1975 Fed. Rep. of Germany .
877830 9/1961 United Kingdom .
1350883 4/1974 United Kingdom .
1359095 7/1974 United Kingdom .
1511645 5/1978 United Kingdom .

OTHER PUBLICATIONS

Seshadri et al, Proc. Ind. Acad. Sci., 17A, pp. 16-19 (1943).

Dean et al, New England Journal of Medicine, vol. 299, pp. 752-763, 804-811 and 863-870 (1978).

Primary Examiner—Dolph H. Torrence

[57] ABSTRACT

This invention is directed to novel ether compounds of formula (I)

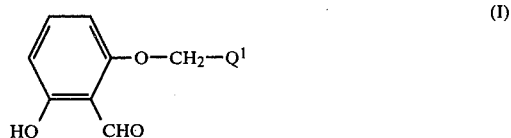

which are of value in medicine in the palliation of haemoglobinopathies, in particular sickle-cell anaemia, and also in the palliation of pulmonary dysfunction, protection from the effects of hypoxia and the radiosensitization of tumors. The invention is also directed to methods for the preparation of the ether compounds, to pharmaceutical formulations containing them, the preparation of such formulations and the use of the compounds in human medicine. Also provided by the invention are intermediates of value in the preparation of the ether compounds, by the methods described, and the preparation of the intermediates.

58 Claims, 1 Drawing Figure

PHARMACEUTICAL ETHERS

This is a continuation of application Ser. No. 163,589 filed June 27, 1980, abandoned.

This invention relates to ethers useful in medicine, to the preparation of such compounds, to pharmaceutical formulations containing such compounds and the preparation of such formulations, to the use of the compounds in medicine, and to novel intermediates for the said compounds and the preparation thereof.

The present invention more particularly relates to the novel ether compounds of formula (I),

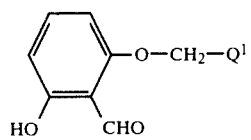

as hereinafter defined, which are of value in medicine in the palliation of haemoglobinopathies including and in particular sickle-cell anaemia.

All adult haemoglobins are composed of four polypeptide (globin) chains, two identified as α and two as non-α, which together comprise the haemoglobin tetramer. Each chain surrounds a porphyrin molecule (haem) containing a central iron atom to which oxygen is reversibly bound. The α and non-α chains have different sequences of amino acid residues and are of slightly different lengths but they have similar three-dimensional structures. In the normal adult (as opposed to neo-natal) human 96 to 97 percent of the non-α chains are β chains that associate with α chains to form the A (adult) haemoglobin tetramer, $\alpha_2\beta_2$, referred to as Hb-A.

The sequences of residues in the chains are genetically determined and thus are inherited characteristics, although the pattern of inheritance is complex with the individual inheriting haemoglobin types from both parents. In consequence of a specific, rare genetic defect the normal β chain is replaced by the abnormal $\beta^s$ chain which associates with α chains to form the sickle haemoglobin tetramer, $\alpha_2\beta_2^s$, referred to as Hb-S. Individuals homozygous for the $\beta^s$ chain gene, i.e. having the SS genotype in which state no Hb-A is present, exhibit sickle-cell anaemia while the sickle-cell trait is manifest in heterozygotes having genes for both the β and $\beta^s$ chains, i.e. the AS genotype, and thus a mixture of Hb-A and Hb-S.

Sickle-cell anaemia is essentially a disease of childhood and symptoms begin to be exhibited in infancy. The major manifestations are a chronic haemolytic anaemia and vaso-occlusive crises that cause severe pain as well as long-term and widespread organ damage, for example isohaemic ulcers, bone infarcts, proliferative retinopathy and cerebral thrombosis. In addition there are systemic effects such as increased susceptibility to infections and impaired growth and development. There is a wide spectrum of clinical severity with many of those affected dying in infancy while for the survivors the course is progressive with death usually occurring before the age of 30. (Individuals with sickle-cell trait appear to have almost no increase in morbidity and mortality although symptons may appear in those inheriting two abnormal haemoglobins, as in sickel cell-haemoglobin C disease and thalassaemia-sickle cell disease).

The responsible genetic mutation has its highest incidence in black Africans and Afro-Americans but is also found in Greece, Italy, Israel, Saudi Arabia and India. In the United States of America the gene frequency has been estimated at 8 to 10 percent in the Black population with about 50,000 homozygous individuals.

The behaviour of the haemoglobin (predominantly Hb-S) in erythrocytes (red blood cells) from sickle-cell anaemia sufferers differs from that of the haemoglobin in erythrocytes from normal adults (predominantly Hb-A) in the following important aspects.

(A) The oxygen-dissociation curve. When a graph is plotted of the percentage saturation of haemoglobin with oxygen (ordinate) against the partial pressure of oxygen, sometimes called the oxygen tension (abscissa) a characteristic sigmoid curve is obtained. With respect to the curve obtained with whole blood from normal adults, that obtained with whole blood from sickle-cell anaemia sufferers is displaced to the right. That is to say, the haemoglobin in the sickle-cell erythrocytes has a reduced oxygen affinity compared with that in the normal erythrocytes, a higher oxygen tension being required to produce a given percentage saturation. (With whole blood from individuals having the sickle-cell trait the curve is not significantly displaced from the normal).

(B) The deoxyhaemoglobin tetramer. When erythrocytes from sickle-cell anaemia sufferers are deoxygenated in vitro under physiological conditions the Hb-S therein aggregates into long 'polymers', non-covalently linked arrays of deoxyHb-S molecules which align themselves into viscous paracrystalline gels also called liquid crystals or tactoids. This deoxygenation-dependent gelation can be observed in the intact erythrocyte by a variety of physical techniques such as optical birefringence and electron microscopy and is accompanied by deformation of the erythrocyte (commonly termed sickling) into characteristic sickle and holly-leaf forms and by a loss of deformability. No such behaviour is observed with erythrocytes from normal adult individuals. The gelation and sickling can be reversed by oxygenation, i.e. conversion of the deoxyHb-S to the oxygenated conformation, except for a proportion identified as irreversibly sickled cells (ISC's) which are characterized by their inability to resume the normal biconcave disc shape even after dissolution of the Hb-S gel.

Although the exact relationships are as yet incompletely understood the gelation, sickling and loss of deformability are known to be involved in the pathophysiology of the disease: typically between 30 and 60 percent of the erythrocytes in venous blood from sickle-cell anaemia sufferers are sickled but in the sickle-cell trait the figure is only of the order of 1 percent.

Because it has its origins in a genetic defect no true cure for sickle-cell anaemia is possible short of genetic manipulation. At present, effective medical intervention is restricted to supportive care of painful and aplastic crises, treatment of infections and therapies directed towards particular organ involvement: blood transfusions (from normal donors) are given prophylactically before surgical operations and childbirth. The prime objective of much current research is a drug that will compensate for the fundamental defect of sickle-cell anaemia but, despite impressive gains in the understanding of the molecular pathogenesis of the disease, as yet no compound has proved to be both sufficiently efficacious and safe to be generally acceptable (for a review see 'Sickle-cell anaemia: Molecular and cellular bases of therapeutic approaches' by J Dean and A N Schechter, *New England Journal of Medicine,* 299 (1978) pp 752–763, 804–811 and 863–870).

The compounds of formula (I), as hereinafter defined, are effective in the palliation of sickle-cell anaemia (i.e. in alleviating the symptoms of the disease and in mitigating the sufferings of those having the condition) and in particular exhibit the following properties:

(A) They induce a left-displacement of the oxygen-dissociation curve of whole normal (AA genotype) human blood in vitro, i.e. the oxygen affinity is increased and the oxygenated conformation of the Hb-A is stabilized.

(B) They induce a left-displacement of the oxygen-dissociation curve of whole rat blood, both in vitro and in vivo.

(C) They induce a left-displacement of the oxygen-dissociation curve of whole homozygous (SS genotype) human sickle-cell blood in vitro.

(D) They prevent the onset of sickling in vitro in whole homozygous human sickle-cell blood and also restore sickled cells to their normal shape.

In formula (I), as set forth above,
$Q^1$ is selected from

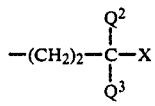

and

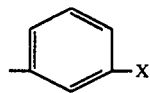

where
$Q^2$ and $Q^3$ are independently selected from hydrogen and alkyl of 1 to 4 carbon atoms, and
X is selected from cyano, carboxyl or a derivative thereof and 5-tetrazolyl,
together with salts thereof.

The alkyl identities for $Q^2$ and $Q^3$ preferably have 1 or 2 carbon atoms (i.e. methyl or ethyl) and are desirably methyl.

A sub-class of compounds within formula (I) are those wherein $Q^1$ is $-(CH_2)_2-CH_2-X$ where X is carboxyl or a derivative thereof or is 5-tetrazolyl, together with salts thereof.

Compounds within formula (I) wherein X is a carboxyl derivative include:

esters, including aliphatic and aromatic hydrocarbon esters such as alkyl and aralkyl esters where for example the alkyl has 1 to 12 and preferably 1 to 4 carbon atoms (in particular methyl, ethyl, isopropyl and t-butyl) and where the aralkyl is for example benzyl; and amides, including the unsubstituted amide, N-substituted amides and N,N-disubstituted amides (embracing cyclic and heterocyclic amides) where the substituent group(s) is (are) for example aliphatic hydrocarbon such as alkyl, in particular alkyl of 1 to 4 carbon atoms such as methyl, ethyl, isopropyl and t-butyl.

In the salts of the compounds of formula (I) the biological activity resides in the ether (anion) moiety and the identity of the cation is of less importance although for use in medicine it is preferably pharmacologically acceptable to the recipient. Suitable salts include ammonium salts, alkali metal salts such as sodium and potassium salts, and salts formed with organic bases.

As a subclass within formula (I) may be mentioned the compounds wherein
X is selected from cyano, 5-tetrazolyl and a group —CO.Y, where
Y is —OR$^1$ and R$^1$ is hydrogen, alkyl of 1 to 4 carbon atoms or benzyl, or
Y is —NR$^2$R$^3$ where R$^2$ and R$^3$ are independently hydrogen or alkyl of 1 to 4 carbon atoms,
together with salts thereof.

As a further subclass within formula (I) may be mentioned the compounds wherein
X is selected from 5-tetrazolyl and a group —CO.Y, where
Y is —OR$^1$ and R$^1$ is hydrogen, alkyl of 1 to 4 carbon atoms or benzyl, or
Y is —NR$^2$R$^3$ where R$^2$ and R$^3$ are independently hydrogen or alkyl of 1 to 4 carbon atoms,
together with salts thereof.

Preferred within formula (I) are those compounds wherein X is carboxyl, together with salts thereof.

Particularly preferred compounds include

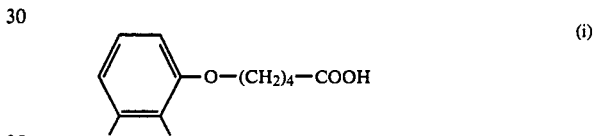

chemically named 5-(2-formyl-3-hydroxyphenoxy)-pentanoic acid,

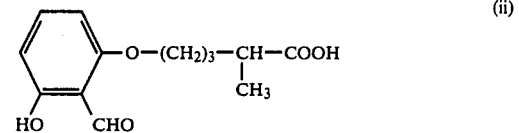

chemically named 5-(2-formyl-3-hydroxyphenoxy)-2-methylpentanoic acid,

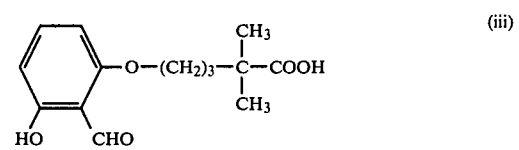

chemically named 5-(2-formyl-3-hydroxyphenoxy)-2,2-dimethylpentanoic acid, and

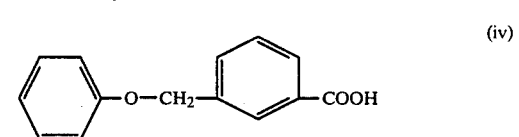

chemically named 3-(2-formyl-3-hydroxyphenoxy)-methylbenzoic acid, together with salts thereof.

Especially preferred of the foregoing is compound (i), 5-(2-formyl-3-hydroxyphenoxy)pentanoic acid (hereinafter referred to as the compound of formula (Ia)) together with salts thereof.

Where the compounds of formula (I), as above defined, include an asymmetric centre the said formula should be understood to include all optical isomers embraced thereby and mixtures thereof.

The compounds of formula (I) and their salts may be prepared by those methods known in the art for the synthesis of compounds of analogous structure and in this regard reference is made, by way of illustration only, to the following standard texts:

(i) "Protective Groups in Organic Chemistry", ed. J. F. W. McOmie, Plenum Press (1973), ISBN 0-306-30717-0;

(ii) "Compendium of Organic Synthetic Methods", ed. I. T. Harrison and S. Harrison, Wiley-Interscience, Vol. I (1971) ISBN 0-471-35550-X, Vol. II (1974) ISBN 0-471-35551-8 and Vol. III (ed. L. S. Hegedus and L. Wade) (1977) ISBN 0-471-36752-4; and (iii) Rodd's "Chemistry of Carbon Compounds", second edition, Elsevier Publishing Company.

All references identified hereinabove or in the following are hereby incorporated herein by reference thereto.

(1) One method comprises reaction of the phenol (II) with an alkane derivative (III)

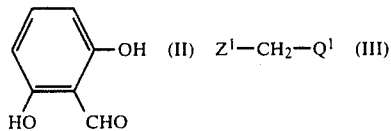

wherein $Q^1$ is as defined in formula (I) and $Z^1$ is a leaving atom or group.

As one possibility $Z^1$ is selected from for example halo (such as bromo, when a catalytic amount of for example sodium iodide is desirably present), arylsulphonyloxy such as p-toluenesulphonyloxy and alkylsulphonyloxy such as methanesulphonyloxy, the reaction being carried out under basic conditions.

The reaction may thus for example be effected in the presence of an alkali metal carbonate such as potassium carbonate, an alkali metal alkoxide such as sodium or potassium ethoxide or an alkali metal hydride such as sodium hydride and in a solvent such as a lower alkanol (for example, ethanol) or an aliphatic ketone (for example, acetone or methylethylketone), and is conducted at elevated temperatures, preferably at the reflux temperature of the reaction mixture. As an alternative, the alkali metal hydride may be employed at ambient temperature in a solvent such as dioxan, tetrahydrofuran, dimethylsulphoxide, acetonitrile, dimethylformamide or dimethylacetamide.

In an alternative procedure (II) is reacted in the presence of triphenylphosphine and diethyl azodicarboxylate with a compound (III) having $Z^1$ as hydroxyl, the reaction being conducted under an inert atmosphere (for example nitrogen or argon) and in a polar aprotic medium.

(2) A further method comprising conversion of an ether (IV)

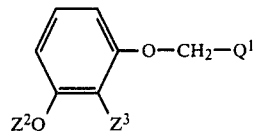

wherein $Q^1$ is as defined in formula (I), $-OZ^2$ is hydroxyl or a group convertible thereto and $Z^3$ is formyl or a group convertible thereto and where $Z^3$ is other than formyl when $-OZ^2$ is hydroxyl, or $-OZ^2$ and $Z^3$ together comprise a ring system that can be selectively cleaved to provide the o-hydroxy-formyl function.

Suitable identities for the moiety $Z^2$ include alkyl, for example alkyl of 1 to 4 carbon atoms and in particular methyl, ethyl, isopropyl and t-butyl; aralkyl such as benzyl; acyl such as alkanoyl, in particular alkanoyl where the alkyl moiety therein has 1 to 4 carbon atoms, for example acetyl; methoxyethoxymethyl; and tetrahydropyranyl. Such groups may be removed, i.e. replaced by hydrogen, by methods standard in the art. Thus removal of an alkyl group may be effected using for example magnesium iodide or sodium thiocresolate or (at reduced temperatures) by use of an agent such as boron trichloride or tribromide in a medium such as dichloromethane; an acyl group may be removed by base hydrolysis; an alkyl group, methoxyethoxymethyl and tetrahydropyranyl may be removed by acid hydrolysis; and hydrogenolysis (for example using a palladium charcoal catalyst) may be used to remove an aralkyl group.

Suitable identities for $Z^3$ include conventional protecting groups for aldehydes such as acetal, thioacetal (mercaptal), oxime, hydrazone (including phenylhydrazone), semicarbazone and anil (Schiff base) functions. The formyl group can be generated therefrom by standard procedures, for example by acid or base hydrolysis or, in the case of thioacetals, by treatment with mercuric chloride in the presence of cadmium carbonate.

As further possible identities for $Z^3$ may be mentioned groups selectively oxidisable to the formyl group. Thus when $Z^3$ is methyl the compound of formula (I) may be obtained by use of chromium trioxide in acetic anhydride with subsequent hydrolysis (for example dilute sulphuric or hydrochloric acid) of the initially formed benzylidene acetate; when $Z^3$ is $-CH_2OH$ suitable reagents include chromium trioxide in pyridine, pyridinium dichromate, pyridinium chlorochromate and manganese dioxide. Other suitable procedures include treatment of the corresponding benzylidene chloride ($Z^3$ is $-CHCl_2$) either with water at elevated temperatures and in the presence of iron powder as catalyst or with boric acid. The compounds of formula (I) may also be derived from the corresponding benzyl chloride ($Z^3$ is $-CH_2Cl$) by refluxing with aqueous copper or lead nitrate in a current of carbon dioxide or alternatively by refluxing with hexamethylenetetramine in aqueous ethanolic solution (Sommelet's reaction).

Further suitable techniques comprise selective reduction to the formyl group of appropriate identities for $Z^3$. In particular may be mentioned reduction of the benzoyl chloride ($Z^3$ is $-COCl$) using hydrogen and a palladium catalyst in the presence of a quinoline-sulphur poison (Rosenmund's reduction); reduction of the nitrile ($Z^3$ is $-CN$) using Raney nickel in formic acid, stannous chloride and hydrochloric acid (Stephen's method) or a reagent such as sodium triethoxyaluminium hydride, prepared from aluminium ethoxide and sodium hydride in ether or tetrahydrofuran; and reduction of an alkyl (for example methyl or ethyl) ester ($Z^3$ is —COOMe/Et) by use of sodium diisobutylaluminium hydride (from sodium hydride and diisobutylaluminium hydride) in ether at $-70°$ C.

As another possibility, an ether (IV) wherein $Z^3$ is the 4-oxazolinyl group may be converted into a compound of formula (I) by treatment with an alkyl iodide, for example methyl iodide, to yield the quaternary N-alkyl compound followed by reduction with an agent such as sodium borohydride.

Suitable compounds within formula (IV) wherein —$OZ^2$ and $Z^3$ together comprise a ring system as above defined include the benzofurans (V) and the 1,3 benzodioxans (VI)

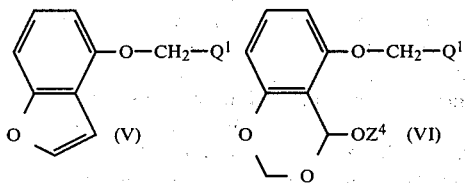

wherein $Q^1$ is as defined in formula (I) and (in(VI)) $Z^4$ is lower alkyl such as methyl or ethyl. Conversion of the benzofurans to the compounds of formula (I) may be effected by ozonolysis and subsequent treatment with zinc dust in acetic acid or by chromic acid hydrolysis, while for the 1,3-benzodioxans acid hydrolysis is appropriate.

(3) For compounds of formula (I) and salts thereof wherein $Q^1$ is a group

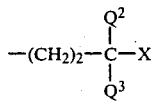

a further method comprises selective reduction of an ether (VII)

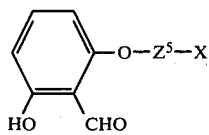

wherein X is as defined in formula (I) and —$Z^5$— is a group selectively reducible to

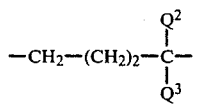

As one possibility —$Z^5$— may be an unsaturated hydrocarbon chain which includes a vinylene or ethynylene group, as in respectively

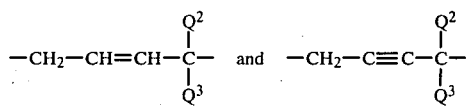

Such groups may be reduced by methods standard in the art, for example a vinylene group by use of hydrogen and a catalyst such as palladium, Raney nickel or Adams' catalyst, while Adams' catalyst may also be used in respect of an ethynylene group.

As another possibility 13 $Z^5$— may include an oxo group, as in

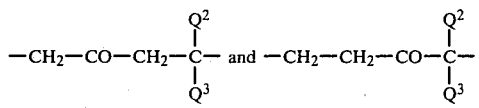

which may be reduced to a methylene group by standard procedures such as the Clemmensen reduction using amalgamated zinc and concentrated hydrochloric acid or by heating with concentrated hydriodic acid and red phosphorus. It will be appreciated that in such circumstances the formyl group in the starting material (VII) may require initial protection and subsequent deprotection for example in the manner indicated in (2) supra.

(4) The compounds of formula (I) and salts thereof may also be prepared by introduction of a formyl group into a phenol (VIII)

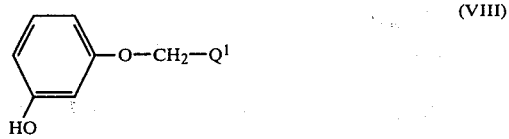

wherein $Q^1$ is as defined in formula (I).

As one possibility this may be effected by lithium exchange with an agent such as phenyllithium and subsequent formylation with for example dimethylformamide, N-methylformanilide or diethylphenyl orthoformate.

As an alternative procedure, those compounds of formula (I) wherein (in the group $Q^1$) X is a group stable under basic conditions (for example, carboxyl and 5-tetrazolyl) may be prepared by the Reimer-Tiemann synthesis, i.e. reaction with chloroform and a base such as pyridine or an alkali metal hydroxide or carbonate.

(5) A further method comprises conversion of a compound of formula (IX)

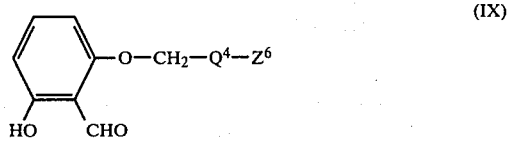

wherein $Z^6$ is a group convertible to a group X as defined in formula (I) and —$Q^4$— is selected, as appropriate, from

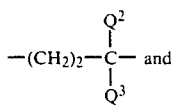

and

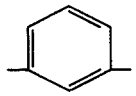

Thus the compounds of formula (I) having X as the 5-tetrazolyl group may be prepared by reacting a compound of formula (IX) wherein $Z^6$ is a tetrazolyl group precursor with hydrazoic acid or a salt thereof or with nitrous acid, as appropriate.

Compounds of formula (IX) wherein $Z^6$ is formyl, —CH$_2$OH or (lower alkyl) alkanoyl such as acetyl may be converted to the carboxyl compounds of formula (I) (X is carboxyl) by standard oxidative procedures using for example acid dichromate: it will be appreciated that in such circumstances the formyl group present in (IX) and retained in the compound of formula (I) may require initial protection and subsequent deprotection, for example in the manner indicated in (2) supra. The acetyl compounds of formula (IX) may also be converted to the carboxyl compounds of formula (I) by means of the haloform reaction. The said carboxyl compounds may also be prepared by hydrolysis of the corresponding acid chlorides and (lower alkyl) mixed anhydrides such as the ethyl compounds ($Z^6$ is —CO.O.CO.Et).

The (lower alkyl) mixed anhydrides of formula (IX) and the acid chlorides may be converted to the esters within formula (I) by reaction with the appropriate alcohol while the amides within formula (I) may be prepared by ammonolysis of the said starting materials using ammonia or a primary or secondary amine, as appropriate.

It will be appreciated that this synthetic approach also embraces the conversion, by standard procedures, of certain of the end-product compounds of formula (I) to other compounds also within the said formula. Thus the esters may be converted to the corresponding carboxyl compounds (carboxylic acids) by hydrolysis, the corresponding salts being obtained when the hydrolysis is carried out with alkali (saponification), and to the amides by ammonolysis using, as appropriate, ammonia or a primary or secondary amine. The amides may also be prepared by treatment of the carboxyl compounds with for example triethylamine and ethyl chloroformate followed by, as appropriate, an ammonium salt or a primary or secondary amine. The unsubstituted amides may also be prepared by treating an ester with sodamide in liquid ammonia, by the action of heat upon the ammonium salts of the carboxylic acids, or by reacting the said acids with urea. The acids and, as appropriate, salts thereof may be prepared by acid or base, preferably base, hydrolysis of an amide or by the action of nitrous acid upon the unsubstituted amides. The esters may be obtained from the acids by esterification using the appropriate alcohol or, for alkyl esters having at least two carbon atoms, by treatment with the appropriate olefin in the presence of boron trifluoride. The alkyl esters may also be prepared by refluxing the silver salts of the acids in ethanol with the appropriate alkyl halide, while the methyl esters may specifically be prepared by treating the acids with diazomethane in ether. Conversion of the benzyl esters to the acids may be effected by hydrogenolysis using for example a palladium charcoal catalyst and conversion of one ester to another is possible using routine transesterification techniques.

The nitriles of formula (I) (X is cyano) may be converted by conventional hydrolysis procedures to the carboxylic acids (X is carboxyl) or, by graded hydrolysis, to the corresponding unsubstituted amides. The said nitriles may also be converted to the corresponding 5-tetrazolyl compounds of formula (I) by reaction with hydrazoic acid or a salt thereof (vid. sup.), the reaction preferably being carried out at elevated temperature with a hydrazoic acid salt such as the ammonium salt and in a polar aprotic medium such as dimethylsulphoxide or dimethylformamide.

(6) A further method comprises decarboxylation of a benzoic acid (X)

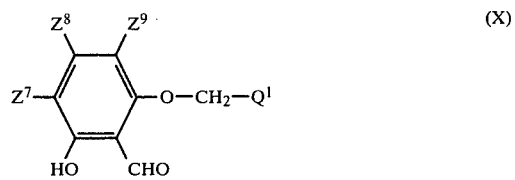

(X)

wherein $Q^1$ is as defined in formula (I) and one of $Z^7$, $Z^8$ and $Z^9$ is carboxyl and the other two are both hydrogen.

The decarboxylation may be effected by any of the conventional techniques, for example by heating (X) in quinoline in the presence of copper or with dioxane and acidic alumina.

Preferred acids (X) are those wherein $Z^7$ is carboxyl and $Z^8$ and $Z^9$ both hydrogen.

The compounds of formula (I) wherein X is carboxyl or 5-tetrazolyl may be isolated as such or as salts thereof and it will be appreciated that the said compounds may be converted to salts thereof, and the reverse, and the salts converted to salts formed with other cations, by techniques well-known and conventional in the art. Thus, those salts which are not themselves pharmacologically acceptable are of value in the preparation of the parent carboxyl or 5-tetrazolyl compounds and of pharmacologically acceptable salts thereof.

When the preparative procedures herein described provide a mixture of optical isomers of a compound of formula (I) or of an intermediate thereto, the individual isomers may be separated by appropriate conventional techniques.

The compounds of formula (I), as above defined, may be used in medicine in the palliation of haemoglobinopathies and in particular for alleviating the symptoms of sickle-cell anaemia and mitigating the sufferings of those having the condition. The compounds may be used both on a regular maintenance basis and for the relief of acute crisis states.

The compounds may be administered to the human recipient by a route selected from oral, parenteral (including subcutaneous, intradermal, intramuscular and intravenous) and rectal. The size of an effective palliative dose of a compound will depend upon a number of factors including the identity of the recipient, the type of haemoglobinopathy involved, the severity of the condition to be treated and the route of administration and will ultimately be at the discretion of the attendant physician. In guiding him in assessing the efficacy and acceptability of a regimen the physician may have recourse not only to changes in the recipient's gross condition but also to in vitro haematological procedures standard in the art, for example those specifically mentioned herein and also the erythrocyte filterability test described in the Dean and Schechter reference supra and in U.S. Pat. No. 4,137,309. Such an effective dose will generally be in the range 1 to 500 mg/kg bodyweight of human recipient per day, preferably in the range 5 to 100 mg/kg bodyweight per day and most preferably in the range 10 to 50 mg/kg bodyweight per day; an optimum dose is 20 mg/kg bodyweight per day. Unless otherwise indicated all weights are calculated as the carboxyl or 5-tetrazolyl acid of formula (I): for the salts, esters, amides and nitriles within the said formula the figures would be amended proportionately. The desired dose is preferably presented as between two and four sub-doses administered at appropriate intervals throughout the day. Thus where three sub-doses are employed each will generally lie in the range 0.33 to 167, preferably 1.67 to 33.3 and most preferably 3.33 to 16.7 mg (acid)/kg bodyweight with an optimum of 6.67 mg (acid)/kg bodyweight. A daily dose for a human weighing of the order of 50 kg will thus generally lie in the range 50 mg. to 25 g (acid), preferably in the range 250 mg. to 5 g (acid) and most preferably in the range 500 mg to 2.5 g (acid) and may be conveniently presented as three equal unit sub-doses of 16.7 mg to 8.33 g (acid), preferably 83.3 mg to 1.67 g (acid) and most preferably 167 mg to 833 mg (acid). Optimally a human daily dose is 1.0 g (acid) conveniently presented as three unit sub-doses each of 333 mg (acid).

While it is possible for the compounds of formula (I) to be administered as the raw chemical it is preferable to present them as a pharmaceutical formulation preparation. The formulations of the present invention comprise a compound of formula (I), as above defined, together with one or more acceptable carriers therefor and optionally other therapeutic ingredients. The carrier(s) must be 'acceptable' in the sense of being compatible with the other ingredients of the formulation and not deleterious to the recipient thereof.

The formulations include those suitable for oral, parenteral (including subcutaneous, intradermal, intramuscular and intravenous) and rectal administration although the most suitable route may depend upon for example the condition of the recipient. The formulations may conveniently be presented in unit dosage form and may be prepared by any of the methods well known in the art of pharmacy. All methods include the step of bringing into association the compound of formula (I) (the active ingredient) with the carrier which constitutes one or more accessory ingredients. In general the formulations are prepared by uniformly and intimately bringing into association the active ingredient with liquid carriers or finely divided solid carriers or both, and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Formulations for rectal administration may be presented as a suppository with the usual carriers such as cocoa butter.

Preferred unit dosage formulations are those containing a daily dose or unit daily sub-dose, as hereinabove recited, or an appropriate fraction thereof, of a compound of formula (I).

It should be understood that in addition to the ingredients particularly mentioned above the formulations of this invention may include other agents conventional in the art having regard to the type of formulation in question, for example those suitable for oral administration may include flavouring agents.

The compounds of formula (I) may also be presented as depot formulations of the kind known in the art from which the active ingredient is released, over a prolonged period, once the formulation is in place within the body of the recipient.

A further application for the compounds of formula (I) is the extracorporeal treatment of blood from the patient. As one possibility such treatment may be conducted in a batch-wise manner by removing an appropriate volume of blood, admixing it with the compound and transfusing the treated blood back into the patient. As an alternative possibility the treatment may be on a continuous basis, analogous to the well-known techniques for haemodialysis, whereby for a period of time blood is continuously withdrawn, admixed with the compound and passed back into the patient. Both procedures should be conducted under sterile conditions and may be repeated as often as necessary: in either case the treatment may be monitored by means inter alia of the in vitro procedures previously mentioned. An effective blood concentration of the compound of formula (I) will generally be in the range 0.1 mM to 100 mM, preferably in the range of 0.3 mM to 33 mM and most preferably in the range 1 mM to 10 mM, with an optimum concentration of 3 mM.

The compounds of formula (I), as above defined, are also of value in the following further areas of human medicine.

(i) The palliation of pulmonary dysfunction, especially in emphysema or chronic bronchitis.

Pulmonary emphysema may be defined in pathological terms as an increase in the size of the air spaces distal to the terminal bronchioles, with destruction of their walls. In clinical practice the disease is associated also with chronic airflow obstruction.

Chronic bronchitis may be defined as chronic or recurrent cough with expectoration which cannot be attributed to conditions other than non-specific lung disease.

(ii) Protection from the effects of hypoxia, for example the hypoxia encountered at high altitude.

(iii) The radiosensitization of tumours (i.e. the tumours are made more sensitive to radiation), as an adjunct to tumour radiotherapy.

For each of these further utilities the compounds of formula (I), as above defined, may be administered to the human recipient by the same routes, at the same doses and sub-doses and as the same pharmaceutical formulations as hereinabove described in respect of their use in the palliation of haemoglobinopathies, although it will be appreciated that the size of an effective dose will again depend upon the same general considerations as indicated hereinabove, namely, the identity of the recipient, the condition involved and its severity and the route of administration, and that the most suitable route may depend for example upon the condition of the recipient. Where it is clinically desirable the compounds may also be used, in the same manner as hereinabove set forth, in the extracorporeal treatment of the patient's blood.

The compounds of formulae (II) to (X) as hereinbefore defined may be prepared by those methods known in the art for the synthesis of compounds of analogous structure: in particular, the compounds of formulae (IV), (V), (VI), (VII), (VIII), (IX) & (X) as hereinbefore defined may be prepared inter alia by methods analogous to those taught herein in respect of the compounds of formula (I) using appropriate starting materials and conditions as hereinbefore described.

It will be understood from the foregoing description that this invention may comprise any novel feature described herein, principally but not exclusively for example:

(a) Compounds of formula (I) as hereinbefore defined.

(b) 5-(2-Formyl-3-hydroxyphenoxy) pentanoic acid and salts thereof.

(c) Methods as hereinbefore described for the preparation of compounds according to (a) or (b) supra, together with the compounds when so prepared.

(d) A pharmaceutical formulation comprising a non-toxic, effective haemoglobiropathy-palliative amount of a compound of formula (I) as hereinbefore defined or a pharmacologically acceptable salt thereof together with an acceptable carrier therefor.

(e) A pharmaceutical formulation comprising a non-toxic, effective haemoglobinopathy-palliative amount of 5-(2-formyl-3-hydroxyphenoxy) pentanoic acid or a pharmacologically acceptable salt thereof together with an acceptable carrier therefor.

(f) A method for the preparation of a formulaton according to (d) or (e) supra comprising admixture of the active ingredient, as defined, with the carrier therefor.

(g) A method for the palliation of a haemoglobinopathy comprising administering to a human having such a condition a non-toxic, effective haemoglobinopathy-palliative amount of a compound of formula (I) as hereinbefore defined or a pharmacologically acceptable salt thereof.

(h) A method for the palliation of a haemoglobinopathy comprising administering to a human having such a condition a non-toxic, effective haemoglobinopathy-palliative amount of 5-(2-formyl-3-hydroxyphenoxy) pentanoic acid or a pharmacologically acceptable salt thereof.

(i) A method according to (g) or (h) supra wherein the haemoglobinopathy is sickle-cell anaemia.

(j) A pharmaceutical formulation comprising a non-toxic, effective pulmonary dysfunction-palliative amount of a compound of formula (i) as hereinbefore defined or a pharmacologically acceptable salt thereof together with an acceptable carrier therefor.

(k) A pharmaceutical formulation comprising a non-toxic, effective hypoxia-protective amount of a compound of formula (I) as hereinbefore defined or a pharmacologically acceptable salt thereof together with an acceptable carrier therefor.

(l) A pharmaceutical formulation comprising a non-toxic, effective tumour radiosensitizing amount of a compound of formula (I) as hereinbefore defined or a pharmacologically acceptable salt thereof together with an acceptable carrier therefor.

(m) A pharmaceutical formulation according to any of (j), (k) and (l) supra comprising 5-(2-formyl-3-hydroxyphenoxy)pentanoic acid or a pharmacologically acceptable salt thereof together with an acceptable carrier therefor.

(n) A method for the preparation of a formulation according to any of (j), (k), (l) and (m) supra comprising admixture of the active ingredient, as defined, with the carrier therefor.

(o) A method for
(i) the palliation of pulmonary dysfunction; or
(ii) protection from the effects of hypoxia; or
(iii) the radiosensitization of a tumour,
comprising administering to a human being requiring such treatment a non-toxic, treatment-effective amount of a compound of formula (I) as hereinbefore defined or a pharmacologically acceptable salt thereof.

(p) A method according to (o) supra comprising administering a non-toxic, treatment-effective amount of 5-(2-formyl-3-hydroxyphenoxy) pentanoic acid or a pharmacologically acceptable salt thereof.

(q) Novel compounds of formulae (II) to (X) as hereinbefore defined, methods for their preparation as hereinbefore described and the compounds when so prepared.

The following Examples are provided in illustration of the present invention and should not be construed as in any way constituting a limitation thereof. All temperatures are in degrees Celsius.

EXAMPLE 1

Preparation of 5-(2-formyl-3-hydroxyphenoxy) pentanoic acid (A) 5-(2-Formyl-3-methoxyphenoxy)pentanoic acid 2-Hydroxy-6-methoxybenzaldehyde (16.875 g., 0.111 M), ethyl 5-bromopentanoate (23.25 g., 17.6 ml., 0.111 M), anhydrous potassium carbonate (16.5 g.), sodium iodide (0.675 g.) and 95% ethanol (150 ml.) were refluxed with stirring (16 hrs). The cooled reaction mixture was filtered and the solid washed well with ethanol. The filtrate was evaporated to dryness and the residue partitioned between ether and water. The ethereal layer was separated and washed with 2 N sodium hydroxide solution, water, dried (sodium sulphate) and evaporated. The residue was dissolved in 95% ethanol (300 ml.) and 0.66 N sodium hydroxide solution (450 ml.) and stirred at ambient temperature (4 hrs). The reaction mixture was evaporated to half volume and diluted with water. The mixture was extracted once with ether and the aqueous layer acidified with concentrated hydrochloric acid with cooling. The crystalline solid formed was filtered off and washed well with water. Recrystallisation from ethyl acetate-petrol gave 5-(2-formyl-3-methoxyphenoxy)pentanoic acid, m.p. 99°–101° C. (Found: C, 61.98; H, 6.58. $C_{13}H_{16}O_5$ requires C, 61.89; H, 6.39%).

(B) 5-(2-Formyl-3-hydroxyphenoxy)pentanoic acid 5-(2-Formyl-3-methoxyphenoxy)pentanoic acid (504 mg., 0.002 M) was dissolved in anhydrous dichloromethane (20 ml.) and cooled to −70° C., with stirring. A solution of boron trichloride in anhydrous dichloromethane (0.25 g/ml., 3.76 ml., 0.94 g, 0.008 M) was added dropwise over 10 mins. and the mixture stirred at −70° C. (15 mins). The reaction mixture was allowed to reach ambient temperature and stirred at that temperature (1.25 hrs). After cooling to 10° C., 10% sodium acetate solution (15 ml.) was added dropwise with stirring so that the temperature did not rise above 15° C. The resulting mixture was diluted with ethyl acetate (50 ml.) and filtered. The filtrate was transferred to a separating funnel and the aqueous layer separated. The organic phase was extracted with 10% sodium carbonate solution (2×50 ml.), the combined extracts acidified with concentrated hydrochloric acid and extracted with ethyl acetate. The combined extracts were washed with water, dried (sodium sulphate) and evaporated to give a crystalline solid. This solid was dissolved in the minimum of chloroform-methanol (95:5) and passed through a pad of Kieselgel G. Evaporation of the filtrate and recrystallisation from benzene-petrol gave 5-(2-formyl-3-hydroxyphenoxy)pentanoic acid, m.p. 97°–99° C. (Found: C, 60.42; H, 6.15. $C_{12}H_{14}O_5$ requires C, 60.50; H, 5.92%).

EXAMPLE 2

Preparation of 5-(2-formyl-3-hydroxyphenoxy)pentanoic acid 5-(2-Formyl-3-methoxyphenoxy)pentanoic acid (Example 1) (25 g, 0.099 M) was dissolved in dry dichloromethane (600 ml) with stirring at −70° C. Boron trichloride (50 g) in dry dichloromethane (100 ml) was then added from a pressure-equalising dropping funnel at such a rate that the temperature of the reaction mixture did not rise above −60° C. (~¼ hr). The mixture was stirred at −70° C. (¼ hr) and then warmed to room temperature by immersion in lukewarm water (~¼ hr). After stirring at room temperature (1 hr) the mixture was carefully poured into 10% sodium acetate solution (500 ml). The resulting mixture was filtered and the layers separated. The aqueous phase was extracted once with dichloromethane and the combined organic solutions evaporated. The residue was dissolved in ethyl acetate/ether (1:1) and extracted with 5% sodium bicarbonate solution (4×250 ml). The combined extracts were acidified with concentrated hydrochloric acid and extracted with ethyl acetate. The combined extracts were washed with water, dried (sodium sulphate) and evaporated. The residue was dissolved in acetone (100 ml) and treated, with swirling, with 40/60 petrol (400 ml). The pale-yellow supernatant solution was decanted from the red tarry residue and filtered. Evaporation gave 5-(2-formyl-3-hydroxyphenoxy)pentanoic acid, m.p. 96°–98° C. from benzene/petrol.

EXAMPLE 3

Preparation of 5-(2-formyl-3-hydroxyphenoxy)pentanoic acid (A) Ethyl 5-(2-formyl-3-benzyloxypheoxy)pentanoate A mixture of 2-hydroxy-6-benzyloxybenzaldehyde (3.0 g, 0.013 M), ethyl 5-bromopentanoate (2.75 g, 0.013 M), anhydrous potassium carbonate (2.16 g, 0.0156 M), sodium iodide (0.195 g) and dry dimethylformamide (15 ml) were stirred at 60°–80° c. for 3 hours and then left to stir at room temperature overnight. The mixture was then poured into water (50 ml) and the product extracted with ether (2×80 ml) and the combined extracts washed with 10% aqueous sodium hydroxide (2×20 ml) and then with water to neutrality, dried, and evaporated to give ethyl 5-(2-formyl-3-benzyloxyphenoxy)-pentanoate, (4.0 g, 86%) as a pale yellow oil.

(B) 5-(2-Formyl-3-benzyloxyphenoxy)pentanoic acid

A mixture of ethyl 5-(2-formyl-3-benzyloxyphenoxy)pentanoate (3.61 g, 0.01 M), potassium hydroxide (1.19 g, 0.021 M) and ethanol (40 ml) were stirred at 50°–60° C. for 5 hours. The ethanol was then removed in vacuo, the residue dissolved in water (50 ml) and the solution extracted with ether (2×80 ml). The aqueous layer was then acidified by the addition of 2 N aqueous hydrochloric acid and the product extracted with ether (3×50 ml), and the combined extracts washed with water to neutrality, dried, and concentrated in vacuo to give 5-(2-formyl-3-benzyloxyphenoxy) pentanoic acid, 3.0 g, 91% as a yellow oil which crystallised on standing. The crude solid was crystallised from benzene/petroleum spirit 30°–40° C. to give pale cream crystals m.p. 110° C.

(C) 5-(2-Formyl-3-hydroxyphenoxy)pentanoic acid

A solution of 5-(2-formyl-3-benzyloxyphenoxy) pentanoic acid (1.0 g, 0.003 M) in ethanol containing 5% palladium on charcoal catalyst (0.61 g) was hydrogenated at atmospheric pressure. After 20 minutes the reaction was complete and the catalyst was filtered off and the ethanol removed in vacuo to give 5-(2-formyl-3-hydroxyphenoxy)pentanoic acid, m.p. 94° C.

EXAMPLE 4

Preparation of 5-(2-formyl-3-hydroxyphenoxy)pentanoic acid (A) Ethyl 5-(2-formyl-3-methoxyphenoxy)pentanoate 2-Hydroxy-6-methoxybenzaldehyde (26.0 g, 0.17 M), ethyl 5-bromopentanoate (27.1 ml, 0.17 M), anhydrous potassium carbonate (25.4 g), sodium iodide (1.04 g) and ethanol (230 ml) were refluxed with stirring for 16 hours. The cooled reaction mixture was filtered and the solid washed well with ethanol. The filtrate was evaporated to dryness and the residue partitioned between ether (200 ml) and water (200 ml). The organic layer was separated and washed with 2 N sodium hydroxide solution (1×150 ml), water (1×150 ml), brine (1×150 ml), dried (magnesium sulphate) and evaporated to yield ethyl 5-(2-formyl-3-methoxyphenoxy)pentanoate 32.97 g, 67% yield, as a pale yellow oil that solidified on standing in the refrigerator.

(B) 5-(2-Formyl-3-hydroxyphenoxy)pentanoic acid 10 ml of a solution of iodine (40.3 g, 0.157 M) in ether (sodium dry, 500 ml) was added to a stirred mixture of magnesium metal (15.4 g, 0.636 G.ATOM) and ether (50 ml). When the reaction had commenced the remainder of the iodine solution was added dropwise at such a rate as to cause gentle refluxing. After the addition was complete the reaction mixture was heated to reflux until a colourless solution was obtained (½ hour). The cooled reaction mixture was filtered and the unreacted magnesium metal was washed with ether (100 ml). The colourless solution of magnesium iodide thus obtained was added dropwise to a solution of ethyl 5-(2-formyl-3-methoxyphenoxy) pentanoate (30.0 g, 0.106 M) in tetrahydrofuran (dried over molecular sieve, 300 ml) at such a rate as to cause gentle refluxing. A fine yellow precipitate dropped out of solution. The mixture was brought to reflux with stirring for 5 hours. The cooled reaction mixture was poured into 10% hydrochloric acid (400 ml). The organic layer was separated and the aqueous layer was extracted with ethyl acetate (2×150 ml). The combined organic phases, containing ethyl 5-(2-formyl-3-hydroxyphenoxy)pentanoate, were washed with water (2×150 ml) and then extracted into 2 N sodium hydroxide solution (3×150 ml). The combined aqueous extracts were acidified with concentrated hydrochloric acid with ice-cooling. The precipitate was filtered, washed with water, sucked dry and then quickly washed with a petrol/ethanol mixture (6:1, 60 ml) to remove some of the colour. The crude product was dried in a desiccator over phosphorus pentoxide to give a dark-peach coloured solid which was then dissolved in ethyl acetate (250 ml); aluminium oxide (neutral, 10 g) and charcoal (5.0 g) were added and the mixture stirred vigourously for ½ hour and then filtered to give a pale-yellow solution. The solvent was removed in vacuo to give 5-(2-formyl-3-hydroxyphenoxy)pentanoic acid, m.p. 98°–99° C. from ethyl acetate/petrol.

EXAMPLE 5

Preparation of 5-(2-formyl-3-hydroxyphenoxy)pentanoic acid

Ethyl 5-(2-formyl-3-methoxphenoxy)pentanoate (Example 4) (2.0 g, 0.00704 M), sodium thiocresolate (2.06 g, 0.014 M), hexamethylphosphoramide (2.48 ml, 0.014 M) and benzene (10 ml) were placed in a round bottom flask and refluxed for 18 hours. The reaction mixture, containing ethyl 5-(2-formyl-3-hydroxyphenoxy)pentanoate, was then cooled and poured into 2 N sodium hydroxide solution (20 ml). The organic layer was removed, diluted with ether (20 ml), then extracted with 2 N sodium hydroxide solution (2×20 ml). The aqueous layers were combined and extracted with dichloromethane (2×20 ml). The organic layer was discarded and the aqueous layer acidified with concentrated hydrochloric acid. The resulting precipitate was filtered, washed with water and dried in a desiccator over phosphorus pentoxide to give 5-(2-formyl-3-hydroxyphenoxy)pentanoic acid, m.p. 98°–99° C. from ethyl acetate/petrol.

EXAMPLE 6

Preparation of 5-(2-formyl-3-hydroxyphenoxy)pentanoic acid (A) Ethyl 5-(2-formyl-3-hydroxy-4-methoxycarbonylphenoxy)-pentanoate Methyl 2,4-dihydroxy-3-formylbenzoate (10.0 g, 0.051 M) was added to dimethylformamide (100 ml), then to this mixture was added sodium hydride (1.344 g, 0.056 M), portionwise. The mixture became warm and effervescence occurred. When the addition was complete the reaction mixture was left to stir at room temperature for 10 minutes. To this solution was then added sodium iodide (0.765 g), ethyl 5-bromovalerate (11.7 g, 0.056 M), and a further 20 ml of dimethylformamide. The whole was brought to 60° C. and left to stir for 5 days. The reaction mixture was cooled, poured into water (200 ml), acidified with concentrated hydrochloric acid, and extracted into ethyl acetate (2×75 ml). The combined organic layers were washed with water (2×75 ml), 5% sodium hydroxide solution (50 ml), water (50 ml) and brine (50 ml), dried (magnesium sulphate), filtered and the solvent removed in vacuo to give ethyl 5-(2-formyl-3-hydroxy-4-methoxycarbonylphenoxy)pentanoate 6.92 g, 42% as a yellow oil, purified by column chromatography and obtained as a pale-yellow solid.

(B) 5-(2-Formyl-3-hydroxy-4-carboxyphenoxy)pentanoic acid

Ethyl 5-(2-formyl-3-hydroxy-4-methoxycarbonylphenoxy)pentanoate (0.5 g, 0.0015 M) was added to 10% sodium hydroxide solution (10 ml) and stirred at room temperature for 2 hours. The reaction mixture was acidified with concentrated hydrochloric acid and the resulting solid was filtered, sucked dry, and washed with a little ethanol, then dried in a desiccator over phosphorus pentoxide to give 5-(2-formyl-3-hydroxy-4-carboxyphenoxy)pentanoic acid, 0.38 g, 90%, m.p. 165°–166° C.

(C) 5-(2-Formyl-3-hydroxyphenoxy)pentanoic acid 5-(2-Formyl-3-hydroxy-4-carboxyphenoxy)pentanoic acid (0.2 g, 0.0007 M), acidic alumina (0.1 g), water (10 ml) and dioxane (3 ml) were left at reflux for 4 days. The reaction mixture was cooled, and made alkaline by the addition of sodium hydroxide. The reaction mixture was filtered and the filtrate acidified with concentrated hydrochloric acid. The resulting precipitate was filtered and washed with a little water, then dried in a desiccator over phosphorus pentoxide to give the title compound as a pale-yellow solid, homogeneous on thin layer chromatography.

EXAMPLE 7

Preparation of 5-(2-formyl-3-hydroxyphenoxy)pentanoic acid 5-(2-Formyl-3-hydroxy-4-carboxyphenoxy)pentanoic acid (Example 6) (0.2 g, 0.0007 M), copper (0.05 g) and quinoline (5 ml) were heated at 210° C. for ½ hour. The reaction mixture was cooled and filtered. Ether (20 ml) was added to the filtrate and the organic layer was washed with 2 N hydrochloric acid (3×20 ml), water (1×20 ml) and brine (1×20 ml), dried (magnesium sulphate) and the solvent removed in vacuo to give 5-(2-formyl-3-hydroxyphenoxy)pentanoic acid as a pale-yellow oil that solidified on standing and was homogeneous on thin layer chromatography (silicagel plates; chloroform:methanol, 10:1).

EXAMPLE 8

Preparation of sodium 5-(2-formyl-3-hydroxyphenoxy)pentanoate 5-(2-Formyl-3-hydroxyphenoxy(pentanoic acid (125 mg, 0.525 mM) was added to a solution of anhydrous sodium bicarbonate (42 mg, 0.5 mM) in water (20 ml). The mixture was warmed gently on the steam bath with swirling (10 minutes), cooled, and excess solid filtered off. The aqueous solution was then freeze-dried. To the solid residue was then added ether and the solid filtered off and washed with ether to give sodium 5-(2-formyl-3-hydroxyphenoxy)pentanoate, 0.66 hydrate.

EXAMPLE 9

Preparation of dicyclohexylammonium 5-(2-formyl-3-hydroxyphenoxy)pentanoate 5-(2-Formyl-3-hydroxyphenoxy)pentanoic acid (119 mg, 0.5 mM) was dissolved in ethyl acetate (5 ml) and cooled to 0° C. under nitrogen with stirring. Dicyclohexylamine (0.11 ml, 100 mg, 0.55 mM) was then added and the mixture stirred at 0° C. (½ hr) under nitrogen. The precipitated solid was then filtered off and washed with ethyl acetate to give dicyclohexylammonium 5-(2-formyl-3-hydroxyphenoxy)pentanoate, 0.25 hydrate, m.p. 114°-115° C.

EXAMPLE 10

Preparation of 5-(2-formyl-3-hydroxyphenoxy)pentanamide 5-(2-Formyl-3-hydroxyphenoxy)pentanoic acid (595 mg, 0.0025 M) was dissolved in dry tetrahydrofuran (5.5 ml) and immersed in a cooling bath kept at $-10°$ C. To the stirred solution under nitrogen was added dropwise from a syringe triethylamine (0.35 ml, 0.0025 M). After 5 minutes was then similarly added ethyl chloroformate (0.25 ml, 0.0025 M). After 15 minutes was then added a solution of ammonium chloride (0.4 g) in water (1.1 ml) and tetrahydrofuran (1.6 ml) previously cooled to 0° C. The vigorously stirred mixture was allowed to come to room temperature over 30 minutes, stirred at room temperature (15 minutes), and then diluted with ether/ethyl acetate (1:1) and 1 N hydrochloric acid. The layers were separated and the organic layer washed with dilute sodium bicarbonate solution and then quickly extracted with 2 N sodium hydroxide (1×25 ml). The layers were separated and the aqueous phase immediately acidified with dilute hydrochloric acid and extracted with ethyl acetate. The combined extracts were washed with dilute sodium bicarbonate solution, water, dried (sodium sulphate) and evaporated to give 5-(2-formyl-3-hydroxyphenoxy)pentanamide, m.p. 94°-95° C. from ethyl acetate/petrol.

EXAMPLE 11

Preparation of N,N-diethyl 5-(2-formyl-3-hydroxyphenoxy)pentanamide 5-(2-Formyl-3-hydroxyphenoxy)pentanoic acid (595 mg, 2.5 mM) was dissolved in dry dichloromethane (7.5 ml) under nitrogen with stirring and immersed in a cooling bath kept at $-10°$ C. To this solution was added dropwise from a syringe triethylamine (0.35 ml, 2.5 mM). After 5 minutes was then similarly added ethyl chloroformate (0.25 ml, 2.5 mM). After 15 minutes was then similarly added diethylamine (0.26 ml, 2.5 mM). The reaction mixture was stirred at $-10°$ C. (10 minutes) and then allowed to warm to 10°-15° C. After diluting with ether (50 ml) and water the aqueous layer was removed and the organic phase washed with dilute sodium bicarbonate solution and then quickly extracted with 2 N sodium hydroxide solution (1×25 ml). The layers were separated and the aqueous phase immediately acidified with dilute hydrochloric acid and extracted with ether/ethyl acetate. The combined extracts were washed with dilute sodium bicarbonate solution, water, dried (sodium sulphate) and evaporated. The oily residue was chromatographed on a short column of kieselgel G (40 g) eluting with chloroform-methanol (95:5) to give N,N-diethyl 5-(2-formyl-3-hydroxyphenoxy)pentanamide as a colourless oil, homogeneous by chromatography (chloroform:methanol, 95:5; Rf 0.35) and having NMR, IR and UV spectra consistent with the assigned structure.

EXAMPLE 12

Preparation of N-isopropyl 5-(2-formyl-3-hydroxyphenoxy)pentanamide 5-(2-Formyl-3-hydroxyphenoxy)pentanoic acid (595 mg, 2.5 mM) was dissolved in dry dichloromethane (7.5 ml) under nitrogen with stirring, and immersed in a cooling bath kept at $-10°$ C. To this solution was added dropwise from a syringe triethylamine (0.35 ml, 2.5 mM). After 5 minutes was then similarly added ethyl chloroformate (0.25 ml, 2.5 mM). After 15 minutes was then similarly added isopropylamine (0.215 ml, 2.5 mM). The reaction mixture was allowed to warm to room temperature and then stirred at room temperature (½ hr). After diluting with ether (50 ml) and 1 N hydrochloric acid the aqueous phase was removed and the organic phase washed with dilute sodium bicarbonate solution and then quickly extracted with 2 N sodium hydroxide solution (1×25 ml). The layers were separated and the aqueous phase immediately acidified with dilute hydrochloric acid and extracted with ether/ethyl acetate. The combined extracts were washed with dilute sodium bicarbonate solution, water, dried (sodium sulphate) and evaporated to give N-isopropyl 5-(2-formyl-3-hydroxyphenoxy)pentanamide, m.p. 92°-93° C. from ethyl acetate/petrol.

EXAMPLE 13

Preparation of ethyl 5-(2-formyl-3-hydroxyphenoxy)pentanoate

To a stirred solution of ethyl 5-(2-formyl-3-methoxyphenoxy)pentanoate (Example 4) (4.38 g, 0.0156 M) in dry tetrahydrofuran (45 ml) was added dropwise a solution of magnesium iodide (6.533 g, 0.0235 M) in dry ether (95 ml). The mixture was then stirred under reflux (5 hr). The cooled mixture was poured into 10% hydrochloric acid (65 ml). The organic layer was separated and the aqueous phase extracted with ethyl acetate. The combined organic solutions were washed with water, dried (sodium sulphate) and evaporated. The oily residue was chromatographed on silica gel eluting with chloroform to give ethyl 5-(2-formyl-3-hydroxyphenoxy)pentanoate, m.p. 32°-33° C.

EXAMPLE 14

Preparation of 5-(2-formyl-3-hydroxyphenoxy)pentanoic acid

Ethyl 5-(2-formyl-3-hydroxyphenoxy)pentanoate (Example 13) (0.5 g, 0.00188 M) was dissolved in 2 N sodium hydroxide solution (10 ml) and stirred at room temperature (30 minutes). The yellow solution was cooled and acidified with concentrated hydrochloric acid and the precipitated solid filtered off and washed well with water to give 5-(2-formyl-3-hydroxyphenoxy)pentanoic acid, m.p. 98°–99° C. from benzene/petrol, identical (NMR spectrum, melting point and mixed melting point) with the end product of Example 4).

EXAMPLE 15

Preparation of 5-(2-formyl-3-hydroxyphenoxy)pentanonitrile (A) 5-(2-Formyl-3-methoxyphenoxy)pentanonitrile 2-Hydroxy-6-methoxybenzaldehyde (3.04 g, 0.02 M), 5-bromopentanonitrile (3.81 g, 0.02 M), anhydrous potassium carbonate (2.97 g), sodium iodide (0.12 g) and ethanol (15 ml) were refluxed with stirring for 4½ hr. The cooled reaction mixture was filtered and the solid washed well with ethanol. The filtrate was evaporated to dryness and the residue partitioned between ether and water. The organic layer was separated and washed with 2 N sodium hydroxide solution water, dried (sodium sulphate) and evaporated to give 5-(2-formyl-3-methoxyphenoxy)pentanonitrile, 2.92 g, 63%, m.p. 71°–72° C. from benzene/petrol.

(B) 5-(2-Formyl-3-hydroxyphenoxy)pentanonitrile

To a stirred solution of 5-(2-formyl-3-methoxyphenoxy)pentanonitrile (2.33 g, 0.01 M) in dry tetrahydrofuran (28 ml) was added dropwise a solution of magnesium iodide (4.17 g, 0.015 M) in dry ether (55 ml). The mixture was then stirred under reflux (5½ hr). The cooled mixture was poured into 10% hydrochloric acid (50 ml). The organic layer was separated and the aqueous phase extracted with ethyl acetate. The combined organic solutions were washed with water and extracted quickly with 2 N sodium hydroxide solution (1×25 ml). The separated aqueous phase was immediately acidified with concentrated hydrochloric acid with cooling and the solid produced filtered off and washed with water to give 5-(2-formyl-3-hydroxyphenoxy)pentanonitrile, m.p. 66°–67° C. from benzene/petrol.

EXAMPLE 16

Preparation of (±)-5-(2-formyl-3-hydroxyphenoxy)-2-methylpentanoic acid (A) (±)-Ethyl 5-(2-formyl-3-methoxyphenoxy)-2-methylpentanoate 2-Hydroxy-6-methoxybenzaldehyde (3.74 g, 0.025 M), ethyl 5-bromo-2-methylpentanoate (5.58 g, 0.025 M), anhydrous potassium carbonate (3.72 g), sodium iodide (0.11 g) and ethanol (50 ml) were refluxed with stirring for 16 hr. The cooled reaction mixture was filtered and the solid washed well with ethanol. The filtrate was evaporated to dryness and the residue partitioned between ether and water. The organic layer was separated and washed with 2 N sodium hydroxide solution, water, dried (sodium sulphate) and evaporated to give (±)-ethyl 5-(2-formyl-3-methoxyphenoxy)-2-methylpentanoate, 5.3 g, 72%, as an oil.

(B) (±)-5-(2-Formyl-3-hydroxyphenoxy)-2-methylpentanoic acid

To a stirred solution of (±)-ethyl 5-(2-formyl-3-methoxyphenoxy)-2-methylpentanoate (5.3 g, 0.018 M) in dry tetrahydrofuran (50 ml) was added dropwise a solution of magnesium iodide (7.44 g, 0.027 M) in dry ether (100 ml). The mixture was then stirred under reflux (5½ hr). The cooled mixture, containing (±)-ethyl 5-(2-formyl-3-hydroxyphenoxy)-2-methylpentanoate, was poured into 10% hydrochloric acid (50 ml), the organic layer was separated and the aqueous phase extracted with ethyl acetate. The combined organic solutions were washed with water and extracted with 2 N sodium hydroxide solution. The combined extracts were acidified with concentrated hydrochloric acid with cooling and the solid produced filtered off and washed with water to give (±)-5-(2-formyl-3-hydroxyphenoxy)-2-methylpentanoic acid, m.p. 70°–70.5° C. from benzene/petrol.

EXAMPLE 17

Preparation of 5-(2-formyl-3-hydroxyphenoxy)-2,2-dimethylpentanoic acid (A) Ethyl 5-(2-formyl-3-methoxyphenoxy)-2,2-dimethylpentanoate 2-Hydroxy-6-methoxybenzaldehyde (3.74 g, 0.025 M), ethyl 5-bromo-2,2-dimethylpentanoate (5.95 g, 0.025 M), anhydrous potassium carbonate (3.72 g), sodium iodide (0.11 g) and ethanol (50 ml) were refluxed with stirring for 18 hr. The cooled reaction mixture was filtered and the solid washed well with ethanol. The filtrate was evaporated to dryness and the residue partitioned between ether and water. The organic layer was separated and washed with 2 N sodium hydroxide solution, water, dried (sodium sulphate) and evaporated to give ethyl 5-(2-formyl-3-methoxyphenoxy)-2,2-dimethylpentanoate, 6.46 g, 84%, as an oil.

(B) 5-(2-Formyl-3-hydroxyphenoxy)-2,2-dimethylpentanoic acid

To a stirred solution of ethyl 5-(2-formyl-3-methoxyphenoxy)-2,2-dimethylpentanoate (6.46 g, 0.021 M) in dry tetrahydrofuran (60 ml) was added dropwise a solution of magnesium iodide (8.67 g, 0.031 M) in dry ether (130 ml). The mixture was then stirred under reflux (5½ hr). The cooled mixture, containing ethyl 5-(2-formyl-3-hydroxyphenoxy)-2,2-dimethylpentanonate, was poured into 10% hydrochloric acid (110 ml). The organic layer was separated and the aqueous phase extracted with ethyl acetate. The combined organic solutions were washed with water, dried (sodium sulphate) and evaporated. The residue was dissolved in 95% ethanol (50 ml) and 2 N sodium hydroxide solution (100 ml) and stirred at room temperature (20 hr). The solution was then evaporated and the residue diluted with water and extracted with ether. The aqueous phase was acidified with concentrated hydrochloric acid with cooling and the solid produced filtered off and washed with water to give 5-(2-formyl-3-hydroxyphenoxy)-2,2- dimethylpentanoic acid, m.p. 76°-77° C. from benzene/petrol.

EXAMPLE 18

Preparation of methyl 3-(2-formyl-3-hydroxyphenoxy)methylbenozate (A) Methyl 3-(2-formyl-3-methoxyphenoxy)methylbenzoate 2-Hydroxy-6-methoxybenzaldehyde (4.56 g, 0.03 M), methyl 3-bromomethylbenzoate (6.87 g, 0.03 M), anhydrous potassium carbonate (4.455 g), sodium iodide (0.18 g) and methanol (50 ml) were refluxed with stirring for 18 hr. The cooled reaction mixture was filtered and the solid washed well with methanol. The filtrate was evaporated to dryness and the residue triturated with 1 N sodium hydroxide solution. The solid was filtered off and washed with water to give methyl 3-(2-formyl-3-methoxyphenoxy)methylbenzoate, 3.27 g, 36%, m.p. 96°-97° C. from ethyl acetate/petrol.

(B) Methyl 3-(2-formyl-3-hydroxyphenoxy)methylbenzoate

To a stirred solution of methyl 3-(2-formyl-3-methoxyphenoxy)methylbenzoate (3 g, 0.01 M) in dry tetrahydrofuran (30 ml) was added dropwise a solution of magnesium iodide (4.13 g, 0.015 M) in dry ether (65 ml). The mixture was then stirred under reflux (5½ hr). The cooled mixture was poured into 10% hydrochloric acid (55 ml). The organic layer was separated and the aqueous phase extracted with ethyl acetate. The combined organic solutions were washed with sodium bicarbonate solution, water, dried (magnesium sulphate) and evaporated. The residue was dissolved in chloroform-methanol (95:5) and filtered through a short pad of florisil. The pale yellow solution was evaporated to give methyl 3-(2-formyl-3-hydroxyphenoxy)methylbenzoate, m.p. 118°-120° C. from ethyl acetate/petrol.

EXAMPLE 19

Preparation of 3-(2-formyl-3-hydroxyphenoxy)methylbenzoic acid

Methyl 3-(2-formyl-3-hydroxyphenoxy)methylbenzoate (Example 18) (500 mg, 0.00175 M) was dissolved in ethanol (5 ml) and 1 N sodium hydroxide solution (5 ml) and stirred at room temperature (2½ hr). The solution was diluted with water and acidified with concentrated hydrochloric acid with cooling and the solid produced filtered off and washed with water to give 3-(2-formyl-3-hydroxyphenoxy)methylbenzoic acid, m.p. 209°-211° C. from ethanol/water.

EXAMPLE 20

Pharmaceutical Formulations

| (A) TABLET | |
|---|---|
| Compound | 300 mg. |
| Lactose | 100 mg. |
| Starch | 50 mg. |
| Polyvinylpyrrolidone | 5 mg. |
| Magnesium Stearate | 5 mg. |
| | 460 mg. |

The Compound, Lactose and Starch are mixed together and then granulated with a solution of Polyvinylpyrrolidone in water. After drying the granules, the Magnesium Stearate is mixed in and tablets compressed at an average weight of 460 mg.

| (B) CAPSULE | |
|---|---|
| Compound | 300 mg. |
| Dibasic Calcium Phosphate, Dihydrate | 100 mg. |
| Sodium Starch Glycolate | 16 mg. |
| Methylcellulose 400 cps | 5 mg. |
| Stearic Acid | 4 mg. |
| Talc | 5 mg. |
| | 430 mg. |

The Compound, Dibasic Calcium Phosphate, Dihydrate and Sodium Starch Glycolate are mixed together and then granulated with a solution of the Methylcellulose in water. After drying, the granules are mixed with the Stearic Acid and Talc and the mixture filled into gelatin capsules at an average fill weight of 430 mg.

| (C) SUPPOSITORY | |
|---|---|
| Compound | 300 mg. |
| Suppository Base (Mixed Glycerides of saturated fatty acids) | 1700 mg. |
| | 2000 mg. |

Grind the Compound to a particle size below 150μ. Add the suppository base at 38°-40° C. Mix to give a uniform dispersion. Pour into suppository moulds and allow to cool.

| (D) INJECTION - Single dose, intravenous | |
|---|---|
| Compound | 300 mg. |
| Sodium Hydroxide Solution (30%) | q.s. |

Water for Injections to 5 ml. Suspend the Compound in some of the Water for Injections. Adjust the pH to 10 to 10.5 by addition of Sodium Hydroxide Solution. Add sufficient Water for Injections to produce the required final volume. Re-check the pH. Sterilise by passage through a sterile membrane filter of 0.22μ pore size. Fill under aseptic conditions into sterile vials and freeze dry.

| (E) INJECTION - Multidose, intramuscular | |
|---|---|
| Compound, sterile | 3000 mg. |
| Polysorbate 20 | 3 mg. |
| Polyvinylpyrrolidone | 1000 mg. |
| Chlorocresol | 60 mg. |
| Sodium Chloride | q.s. to isotonicity |
| Water for Injections to | 30 ml. |

Dissolve the Polysorbate 20, Polyvinylpyrrolidone, Sodium Chloride and Chlorocresol in Water for Injections. Sterile filter, 0.22μ. Grind the sterile Compound to a particle size below 20μ and add to the filtered solution. Mix until a uniform dispersion is achieved. Fill into sterile glass vials.

| (F) PROLONGED RELEASE TABLET | |
|---|---|
| Compound | 600 mg. |
| Casein | 195 mg. |
| Hydrogenated Castor Oil | 400 mg. |

| -continued |   |
| --- | --- |
| (F) PROLONGED RELEASE TABLET | |
| Magnesium Stearate | 5 mg. |
| | 1200 mg. |

Melt the Hydrogenated Castor Oil and add the Compound, ground to a particle size of less than 150μ. Add the Casein. Mix until uniform. Allow to cool and mill to a granule. Mix in the Magnesium Stearate and compress to an average weight of 1,200 mg.

In the foregoing the "Compound" refers to a compound of formula (I) as hereinbefore defined, the weight thereof being calculated as the appropriate carboxyl or 5-tetrazolyl acid as hereinbefore described.

EXAMPLE 21

Pharmacological activity of 5-(2-formyl-3-hydroxyphenoxy)pentanoic acid (compound Ia)

(A) Effect on the oxygen-dissociation curve of whole normal human blood in vitro Compound (Ia) was dissolved in isotonic saline containing sodium bicarbonate 25 mM. To 0.9 ml of fresh, heparinized normal human blood was added 0.1 ml of solution of the compound to give final concentrations of the latter of 0 (control), 0.3, 1.0 and 3.0 mM. The mixtures were incubated (30 mins, 37° C.) and the oxygen-dissociation curve for each then measured using a whole-blood spectrophotometer (Hem-O-Scan, Trade Name). A dose-related left-displacement of the dissociation curve was observed as illustrated by the following results wherein p50 denotes the oxygen tension at which 50% of the haemoglobin is in the oxygenated conformation.

| Compound (Ia) (mM) | Mean p50 (mm. Hg) |
| --- | --- |
| 0 | 26.0 |
| 0.3 | 25.5 |
| 1.0 | 21.5 |
| 3.0 | 9.0 |

(B) Effect on the oxygen-dissociation curve of whole rat blood in vitro

Blood (6.5 ml) from an adult albino rat, exsanguinated via the abdominal aorta under ether anaesthesia, was mixed with acid-citratedextrose anticoagulant (1.5 ml). A 2 ml sample of the mixture was used as a control and compound (Ia) was dissolved in the plasma fraction of a further 2 ml sample to give a final concentration of 3 mM. Both samples were incubated (30 mins, 37° C.) and the oxygen-dissociation curve of each measured as in (A). The curve obtained with the test sample was considerably left-displaced as compared with that obtained with the control.

| Compound (Ia) (mM) | Mean p50 (mm. Hg) |
| --- | --- |
| 0 | 44.5 |
| 3.0 | 8.2 |

(C) Effect on the oxygen-dissociation curve of whole rat blood in vivo

Female albino rats (100–120 g) were fasted for 24 hrs with water available ad lib. Compound (Ia) was dissolved in isotonic saline containing sodium bicarbonate 25 mM and administered to two rats orally (500 mg/kg) and to two rats intravenously (100 mg/kg): appropriate vehicle controls were administered simultaneously to control animals. After 1 hour all animals were exsanguinated via the abdominal aorta under chloroform anaesthesia: 2.5 ml of blood from each was mixed with disodium edetate (anticoagulant) and the oxygen-dissociation curve of each sample measured as in (A). A considerable left-displacement of the curve, as compared with the appropriate control, occurred in each test group.

| Treatment | Mean p50 (mm. Hg) |
| --- | --- |
| Vehicle p.o. | 42.75 |
| *500 mg/kg p.o. | 10.25 |
| Vehicle i.v. | 43.37 |
| *100 mg/kg i.v. | 22.37 |

*Compound (Ia)

The accompanying FIG. 1 shows the curve obtained with compound (Ia) upon intravenous administration as above described together with the corresponding control curve: a curve of similar shape to the former was observed upon oral administration of the compound.

(D) Effect on the oxygen-dissociation curve of whole homozygous human sickle-cell blood in vitro Homozygous human sickle-cell blood (4 vols) was mixed with acid-citrate-dextrose anticoagulant (1 vol) and a portion of the mixture set aside as a control. Compound (Ia) was dissolved in the plasma fraction of the remainder to give a final concentration of 3 mM and both test and control samples incubated at 37° C. for a minimum of 45 mins before measuring the oxygen-dissociation curve of each as in (A). The means of results obtained with three patients are given below, showing the considerable left-displacement seen in the test samples.

| Compound (Ia) (mM) | Mean p50 (mm. Hg) |
| --- | --- |
| 0 | 51 |
| 3.0 | 10 |

(E) Effect on sickling in vitro of whole homozygous human sickle-cell blood

Homozygous human sickle-cell blood was deoxygenated in vitro to an oxygen tension of about 28 mm Hg: approximately 50% of the erythrocytes were sickled under these conditions. After addition of compound (Ia) (3.0 mM) the proportion of sickled cells fell progressively over the next 60 mins to about 3%. In parallel controls the proportion of sickled cells was found to increase over the same period to nearly 70%.

(F) Toxicity data

The acute oral $LD_{50}$ in mice of compound (Ia), administered as a solution in sodium bicarbonate-saline, was found to be approximately 1.0 g/kg.

(G) Cardiovascular effects in anaesthetized rats

Male Wistar rats weighing between 250–350 g were used. Anaesthesia was induced with 3–5% halothane in oxygen and maintained with a mixture of chloralose (60 mg/kg i.v.) and pentobarbitone (20 mg/kg i.v.). A femoral vein was cannulated for the administration of drugs and the ipsilateral femoral artery for measuring arterial blood pressure; heart rate was derived from the femoral pulse by a cardiotachometer. Body temperature was maintained at 38° C.

Five test rats were each given a series of increasing doses of compound (Ia) as a solution in 10%-saturated sodium bicarbonate (saturated sodium bicarbonate solution diluted 1:9). Sufficient time was allowed between doses for the variables to return either to the pre-dose level or to a steady state if full recovery was not attained. Measurements were made 2 mins. after dose or at maximum effect.

Control rats (3) were given a series of 0.2 ml. injections of the sodium bicarbonate vehicle (up to 15 injections) to assess any effect of sodium bicarbonate and of increasing extracellular fluid volume on blood pressure and heart rate.

In the test rats compound (Ia) produced no appreciable change in systolic, diastolic or mean blood pressures up to a dose of 16 mg/kg. Significant dose-dependent falls in pressure were observed at doses of 32–128 mg/kg. Blood pressure recovered within 15 mins. after each dose of test compound. Although no marked changes in heart rate were recorded, there was a slight tachycardia in three rats after the 64 mg/kg dose, but this effect was not statistically significant.

Control rats showed no appreciable change in any of the variables measured.

EXAMPLE 22

Anti-sickling potency in vitro

In an aerated sample of whole homozygous human sickle cell blood, i.e. one maintained at an oxygen tension of 150 mm. Hg, the proportion of normal discoid erythrocytes is usually greater than 90%. If the oxygen tension is reduced the proportion of normal cells decreases because there is an inverse increase in the proportion of sickle and bizarre cells and at an oxygen tension of 28 mm. Hg the proportion of normal cells lies in the range 45–65%. In the presence of an effective concentration of an anti-sickling agent the proportion of normal cells at such low oxygen tensions is increased.

A suitable index of the in vitro anti-sickling potency (ASP) of a compound in whole homozygous human sickle cell blood may be calculated from the $$ASP = 100 \times \frac{(\% \text{ in test}) - (\% \text{ in control})}{(\% \text{ in aerated}) - (\% \text{ in control})}$$

wherein
"control" refers to blood samples maintained under a reduced oxygen tension (28 mm. Hg);
"test" refers to blood samples maintained at 28 mm. Hg as for "control" samples but containing a known concentration of test compound;
"aerated" refers to blood samples maintained at high oxygen tension (150 mm. Hg); and
the percentages refer to the proportion of normal discoid erythrocytes.

The potencies for a number of compounds are presented in the following table. A figure of less than 20 indicates that the compound is essentially inactive (at the test concentration) in this procedure while a negative number denotes an increase in sickling in the presence of the compound.

| Compound | Anti-sickling potency | | |
|---|---|---|---|
|  | 1.0mM | 3.0mM | 10.0mM |
| Example 1 | 82 | 105 |  |
| Example 16 | 88 |  |  |
| Example 17 | 83 |  |  |
| Example 19 | 76 |  |  |
| (A)* |  |  | 52 |
| (B)* |  | −26 |  |
| (C)* |  | −7 |  |

*These compounds have been taught in the literature as of value in the palliation of sickle-cell anaemia, as follows:
(A): Potassium cyanate (see inter alia the Dean and Schechter reference supra)
(B): 3,4-Dihydro-2,2-dimethyl-2H—1 benzopyran-6-butyric acid (Nature, 258, December 25, 1975, 743–746)
(C): Methylenebisphosphonic acid (U.S. Pat. No. 4 137 309)

What is claimed is:

1. A compound of formula (I)

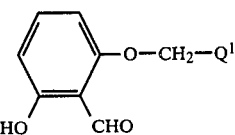

(I)

wherein $Q^1$ is selected from

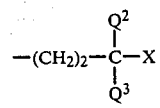

and

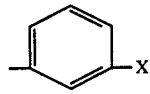

where $Q^2$ and $Q^3$ are independently selected from hydrogen and alkyl of 1 to 4 carbon atoms, and X is selected from cyano, carboxyl and 5-tetrazolyl; salts thereof and, when X is carboxyl, esters and amides thereof, 2. A compound of formula (I)

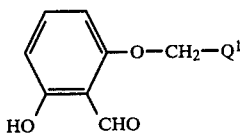

(I)

wherein $Q^1$ is $-(CH_2)_2-CH_2-X$ where X is carboxyl or 5-tetrazolyl; salts thereof and, when X is carboxyl, esters and amides thereof.

3. A compound as in claim 1 wherein X is selected from cyano, 5-tetrazolyl and a group —CO.Y, where
   Y is —OR$^1$ and R$^1$ is hydrogen, alkyl of 1 to 4 carbon atoms or benzyl, or Y is —NR$^2$R$^3$ where R$^2$ and R$^3$ and independently hydrogen or alkyl of 1 to 4 carbon atoms;
and salts thereof.

4. A compound as in claim 3 wherein Q$^1$ is

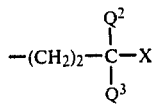

where Q$^2$ and Q$^3$ are independently selected from hydrogen and alkyl of 1 to 4 carbon atoms, and salts thereof.

5. A compound as in claim 3 wherein Q$^1$ is

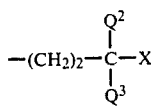

where Q$^2$ and Q$^3$ are independently selected from hydrogen and methyl, and salts thereof.

6. A compound as in claim 3 wherein Q$^1$ is

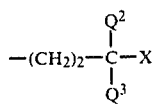

where Q$^2$ and Q$^3$ are both hydrogen, and salts thereof.

7. A compound as in claim 3 wherein Q$^1$ is

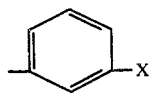

and salts thereof.

8. A compound as in claim 3 wherein X is cyano.
9. A compound as in claim 3 wherein X is —CO.Y where Y is —OR$^1$ and R$^1$ is hydrogen, and salts thereof.
10. A salt of a compound as in claim 3.
11. A pharmacologically acceptable salt of a compound as in claim 3.
12. A compound as in claim 2 wherein X is selected from 5-tetrazolyl and a group —CO.Y, where
    Y is —OR$^1$ and R$^1$ is hydrogen, alkyl of 1 to 4 carbon atoms or benzyl, or
    Y is —NR$^2$R$^3$ where R$^2$ and R$^3$ are independently hydrogen or alkyl of 1 to 4 carbon atoms;
    and salts thereof.
13. A salt of a compound as in claim 12.
14. A pharmacologically acceptable salt of a compound as in claim 12.
15. 5-(2-Formyl-3-hydroxyphenoxy)-2-methylpentanoic acid and salts thereof.
16. 5-(2-Formyl-3-hydroxyphenoxy)-2,2-dimethylpentanoic acid and salts thereof.
17. 3-(2-Formyl-3-hydroxyphenoxy)methylbenzoic acid and salts thereof.
18. A pharmacologically acceptable salt of the acid of claim 15.
19. A pharmacologically acceptable salt of the acid of claim 16.
20. A pharmacologically acceptable salt of the acid of claim 17.
21. 5-(2-Formyl-3-hydroxyphenoxy)pentanoic acid or a salt thereof.
22. A salt of the acid of claim 21.
23. A pharmacologically acceptable salt of the acid of claim 21.
24. An alkali metal salt of the acid of claim 21.
25. 5-(2-Formyl-3-hydroxyphenoxy)pentanoic acid.
26. The compound of claim 3 which is 5-(2-formyl-3-hydroxyphenoxy)pentanonitrile.
27. The compound of claim 12 which is ethyl 5-(2-formyl-3-hydroxyphenoxy)pentanoate.
28. A pharmaceutical formulation comprising a compound of formula (I)

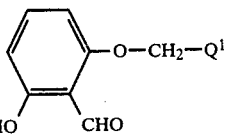 (I)

wherein Q$^1$ is selected from

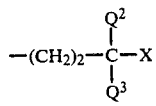

and

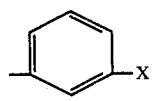

where Q$^2$ and Q$^3$ are independently selected from hydrogen and alkyl of 1 to 4 carbon atoms, and X is selected from cyano, carboxyl and 5-tetrazolyl, a pharmacologically acceptable salt thereof or, when X is carboxyl, an ester or an amide thereof, together with an acceptable carrier therefor.

29. A pharmaceutical formulation comprising a compound of formula (I)

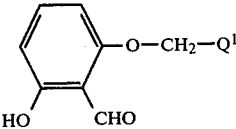 (I)

wherein

Q$^1$ is —(CH$_2$)$_2$—CH$_2$—X where X is carboxyl or 5-tetrazolyl, a pharmacologically acceptable salt thereof or, when X is carboxyl, an ester or an amide thereof, together with an acceptable carrier therefor.

30. A formulation as in claim 28 wherein X is selected from cyano, 5-tetrazolyl and a group —CO.Y, where
    Y is —OR$^1$ and R$^1$ is hydrogen, alkyl of 1 to 4 carbon atoms or benzyl, or
    Y is —NR$^2$R$^3$ where R$^2$ and R$^3$ are independently hydrogen or alkyl of 1 to 4 carbon atoms, or a pharmacologically acceptable salt thereof.

31. A formulation as in claim 29 wherein X is selected from 5-tetrazolyl and a group —CO.Y, where Y is —OR¹ and R¹ is hydrogen, alkyl of 1 to 4 carbon atoms or benzyl, or Y is —NR²R³ where R² and R³ are independently hydrogen or alkyl of 1 to 4 carbon atoms, or a pharmacologically acceptable salt thereof.

32. A pharmaceutical formulation comprising 5-(2-formyl-3-hydroxyphenoxy)pentanoic acid, or a pharmacologically acceptable salt thereof, together with an acceptable carrier therefor.

33. A pharmaceutical formulation comprising 5-(2-formyl-3-hydroxyphenoxy)pentanoic acid together with an acceptable carrier therefor.

34. A formulation as in any one of claims 30, 31, 32 or 33 which is suitable for oral administration.

35. A formulation as in any one of claims 30, 31, 32 or 33 which is suitable for parenteral administration.

36. A formulation as in any one of claims 30, 31, 32 or 33 which is suitable for rectal administration.

37. A formulation as in any one of claims 30, 31, 32 or 33 which comprises the compound or salt in solution in an aqueous medium.

38. A formulation as in any one of claims 30, 31, 32 or 33 in unit dosage form containing a non-toxic amount of the compound or salt.

39. A formulation as in any one of claims 30, 31, 32 or 33 in the form of a tablet suitable for oral administration containing a non-toxic amount of the compound or salt.

40. A formulation as in any one of claims 30, 31, 32 or 33 in the form of a capsule suitable for oral administration containing a non-toxic amount of the compound or salt.

41. A formulation as in any one of claims 30, 31, 32 or 33 in the form of a sterile injection solution suitable for parenteral administration containing a non-toxic amount of the compound or salt.

42. A formulation as in any one of claims 30, 31, 32 or 33 in unit dosage form containing from 500 mg to 2.5 g (calculated as the corresponding acid) of the compound or salt.

43. A formulation as in any one of claims 30, 31, 32 or 33 in unit dosage form containing from 167 mg to 833 mg (calculated as the corresponding acid) of the compound or salt.

44. A method for the palliation of a haemoglobinopathy in a human being having such a condition which comprises administering to said human being a non-toxic, effective palliative amount of a compound as in any one of claims 3, 12 or 25 or a pharmacologically acceptable salt thereof.

45. A method as in claim 44 wherein the haemoglobinopathy is sickle-cell anaemia.

46. A method for the palliation of pulmonary dysfunction in a human being having such a condition which comprises administering to said human being a non-toxic, effective pallative amount of a compound as in any one of claims 3, 12 or 25 or a pharmacologically acceptable salt thereof.

47. A method as in claim 46 for the palliation of pulmonary emphysema.

48. A method as in claim 46 for the palliation of chronic bronchitis.

49. A method for protecting a human being requiring such treatment from the hypoxic effects of high altitude which comprises administering to said human being a non-toxic, effective protective amount of a compound as in any one of claims 3, 12 or 25 or a pharmacologically acceptable salt thereof.

50. A method for the radiosensitization of a tumour in a human being which comprises administering to a human being having a tumour a non-toxic, effective radiosensitizing amount of a compound as in any one of claims 3, 12 or 25 or a pharmacologically acceptable salt thereof.

51. Ethers of the formula

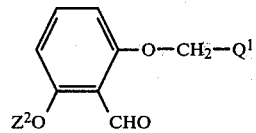

wherein Q¹ is selected from

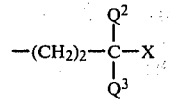

and

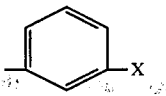

where
Q² and Q³ are independently selected from hydrogen and alkyl of 1 to 4 carbon atoms and
X is selected from cyano, carboxyl and 5-tetrazolyl; and
Z² is alkyl;
salts of said compounds and, when X is carboxyl, esters and amides thereof.

52. The compound of claim 51 which is ethyl 5-(2-formyl-3-methoxyphenoxy)pentanoate.

53. The compound of claim 51 which is 5-(2-formyl-3-methoxyphenoxy)pentanoic acid or a salt thereof.

54. A method for the palliation of a haemoglobinopathy in a human being having such a condition which comprises administering to said human being a non-toxic, effective palliative amount of the pharmaceutical formulation of claim 32.

55. A method for the palliation of pulmonary dysfunction in a human being having such a condition which comprises administering to said human being a non-toxic, effective palliative amount of the pharmaceutical formulation of claim 32.

56. The method of claim 55 in which the pulmonary dysfunction is pulmonary emphysema.

57. The method of claim 55 in which the pulmonary dysfunction is chronic bronchitis.

58. The method of claim 54 in which the haemoglobinopathy is sickle-cell anaemia.

* * * * *